United States Patent [19]

Nicholson-Weller

[11] Patent Number: 5,109,114
[45] Date of Patent: Apr. 28, 1992

[54] CHARACTERIZATION AND METHOD OF ISOLATION FOR AN INHIBITOR OF COMPLEMENT C1

[75] Inventor: Anne Nicholson-Weller, Wellesley, Mass.

[73] Assignee: Beth Israel Hospital, Boston, Mass.

[21] Appl. No.: 406,144

[22] Filed: Sep. 12, 1989

[51] Int. Cl.$^5$ .............................................. C07K 15/06
[52] U.S. Cl. ..................................... 530/350; 530/380
[58] Field of Search ................................. 530/380, 350

[56] References Cited

U.S. PATENT DOCUMENTS

| | | | |
|---|---|---|---|
| 4,147,801 | 4/1979 | Lenhard et al. | 424/315 |
| 4,388,232 | 6/1983 | Eibl et al. | 530/380 |
| 4,883,784 | 11/1989 | Kaneko | 514/8 |
| 4,915,945 | 4/1990 | Pelzer et al. | 421/101 |

OTHER PUBLICATIONS

Lopez-Trascaso et al. 1989, J. Biol. Chem. 264(27): 16214-16221.
Abstract, Biosis Number 62064952 of Cheung et al., 1986, Biochem Biophys Acta, 882(2): 200-209.
Shebrehiwet et al., 1988, J. Immunol. Methods, 110: 251-260.
Silvestri et al., 1981, J. Biol. Chem. 256(14): 7383-7387.
Cooper, "The Classical Complement Pathway: Activation and Regulation of the First Complement Component", 37 Adv. Immunol 151-216 (1985).
Schumaker et al., "Activation of the First Component of Complement", 5 Ann. Rev. Immunol. 21-42 (1987).
Reid et al., "The Proteolytic Activation Systems of Complement", 50 Ann. Rev. Biochem. 433-464 (1981).
Ziccardi, "The Role of Immune Complexes in the Activation of the First Component of Human Complement", 132 J. Immunol. 283-288 (1984).
Ziccardi, "Demonstration of the Interaction of Native C1 with Monomeric Immunoglobulins and C1 Inhibitor", 134, J. Immunol, 2559-2563 (1985).
Ghebrehiet, "C1q Inhibitor (C1qINH): Functional Properties and Possible Relationship to a Lymphocyte Membrane-Associated C1q Precipitin", 126 J. Immunol. 1837-1842 (1981).
Ghebrehiwet, "Purification and Partial Characterization of a C1q Ihhibitor from the Membranes of Human Peripheral Blood Lymphocytes", 129 J. Immunol. 151-162 (1982).
Davis, "C1 Inhibitor and Hereditary Angioneurotic Edema", 6, Ann. Rev. Immunol. 595-628 (1988).

Primary Examiner—Margaret Moskowitz
Assistant Examiner—Keith C. Furman
Attorney, Agent, or Firm—Lorusso & Loud

[57] ABSTRACT

A purified protein, factor J, which has inhibitory properties which prevent the formation or the dissociation of C1 complex and a method of purification for said protein. The method including the following sequential chromatography steps: anion exchange, QAE-Sephadex, heparin-Sepharose affinity, Mono-Q and hydroxylapatite.

3 Claims, 6 Drawing Sheets

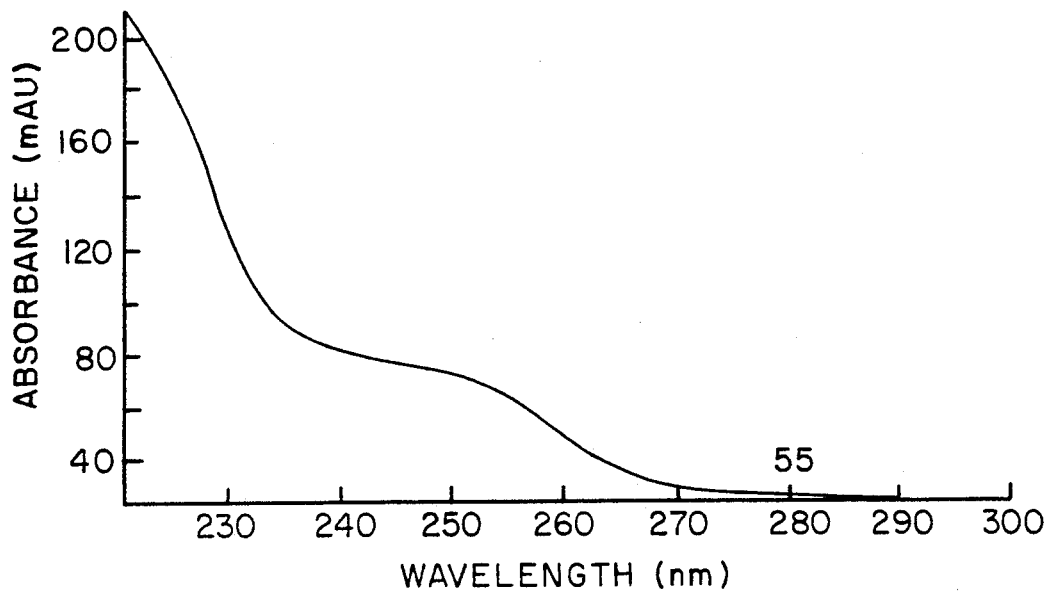
FIG. 3
FIG. 4
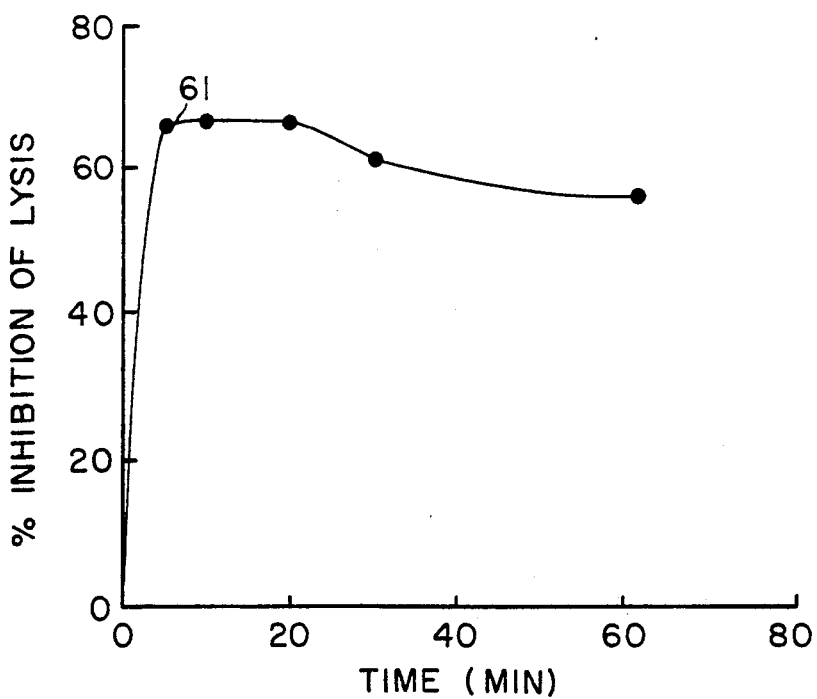

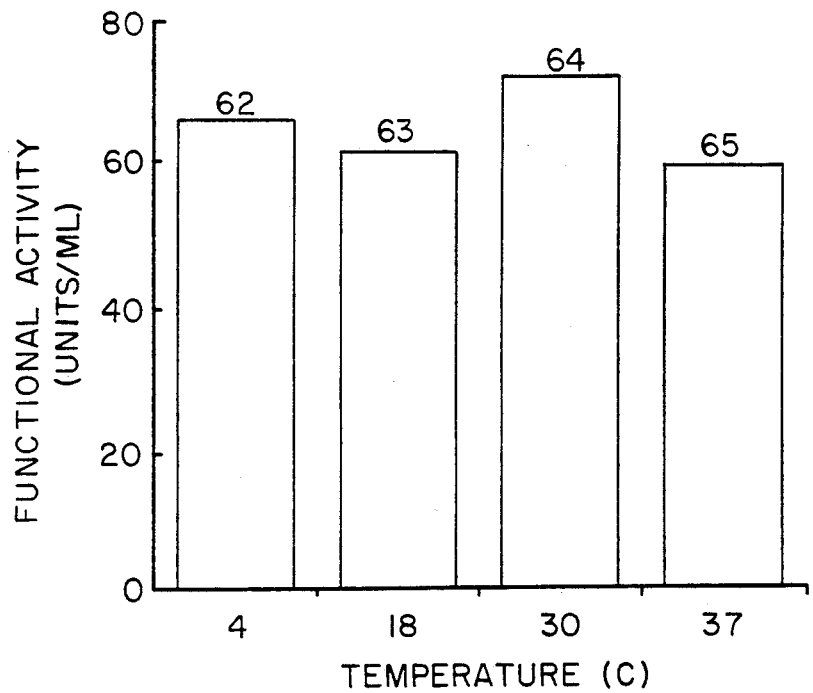
FIG. 5
FIG. 6
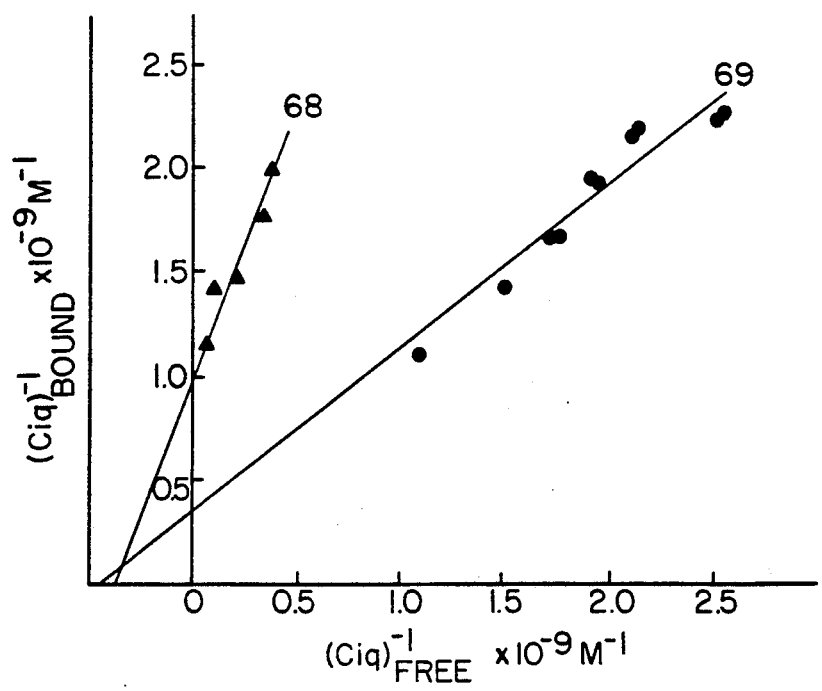

CHARACTERIZATION AND METHOD OF ISOLATION FOR AN INHIBITOR OF COMPLEMENT C1

BACKGROUND OF THE INVENTION

The invention described herein was made with Government support and the U.S. Government has certain rights in the invention.

The immune system is the power of the body to resist invasion by pathogenic organisms, and to overcome such invasion and its ensuing infection, once it has taken place. The complement system is important in the immune response. Complement is a physiological process which involves many plasma proteins that react in a cascading (sequential) effect to mediate a number of desirable biologically significant phenomena. Such phenomena include modulation of the immune response, facilitation of the transport of immune complexes, production of anaphylatoxins which cause release of histamine, chemotaxis which is the migration of cells towards the area of complement activity, phagocytosis, and lysis of cells.

The activation of the complement cascade can also cause undesirable phenomena, such as inflammation, damage of normal tissue and disease states such as the autoimmune diseases. Autoimmune diseases are associated with the immune complexes formed against indigenous tissue which are associated with the biologically active complement fragments generated by the classical portion of the complement cascade. Such diseases include but are not limited to: Hashimoto's thyroiditis, systemic lupus erythematosis, Goodpasture's syndrome, Graves' disease, myasthenia gravis, insulin resistance, autoimmune hemolyic anemia, autoimmune thrombocytopenic prupura, and rheumatoid arthritis.

It is known that the first phase of complement activation begins with C1. C1 is made up of three distinct proteins: a recognition subunit, C1q, and the serine proteinase subcomponents, C1r and C1s which are bound together in a calcium-dependent tetrameric complex, $C1r_2s_2$. An intact C1 complex is necessary for physiological activation of C1 to result. Activation occurs when the intact C1 complex binds to immunoglobulin complexed with antigen. This binding activates C1s which would then react with the next plasma protein, C4, to start the cascading effect rolling.

In terms of the regulation of the complement system, most studies have focused on the binding properties of the C1 serine proteinase subcomponents, C1r and C1s, for a serum glycoprotein, C1 Inhibitor. Another inhibitor that has been identified but whose role in regulating C1 function in plasma is not clear is the C1q inhibitor (C1qINH).

It is important to identify and isolate inhibitors of the complement system because by isolating an inhibitor one may be able to control the effects of diseases such as those stated above. The inhibitors may provide a basis for pharmacologic intervention, either by allowing manipulation of the level of an inhibitor, or by providing a model for the chemical synthesis of a new inhibitor.

It is therefore an object of the present invention to provide a method for the isolation of an inhibitor of C1 which is functionally and antigenically distinct from known inhibitors of C1.

It is more specifically an object of the present invention to characterize the properties of an inhibitor of C1, factor J.

SUMMARY OF THE INVENTION

In accordance with the present invention, factor J is isolated from body fluid, in a multi-column purification procedure. The sequence of columns necessary for purification is an anion exchange, QAE-Sephadex, affinity, Mono Q, and hydroxylapatite HPLC columns. The purified Factor J has a molecular weight (Mr) of about 20,000 daltons, minimal absorption at 280 nm, and a relatively small number of tyrosine residues. The newly discovered protein has been found to inhibit the association of the tetrameric complex $C1r_2s_2$ with the recognition subunit C1q, and it can dissociate the fully assembled-activated C1 complex.

This inhibitor is functionally and antigenically distinct from other known inhibitors of C1, namely, C1INH and C1qINH. The inhibitory capabilities of C1 Inhibitor are the result of its binding to the catalytic subunits of C1, C1r and C1s, and thereby inhibiting C1r and C1s. The C1q Inhibitor can only inhibit the assembly of the C1 complex by prior binding to C1q. In contradistinction, it has been discovered that factor J does not inhibit C1s, and that factor J can both dissociate intact C1 as well as prevent its assembly from subcomponents. Thus, factor J is functionally distinct from C1 Inhibitor and C1q Inhibitor.

In its broadest overall aspect, factor J is first isolated and purified and then administered in a therapeutic amount to inhibit the undesirable activation of the complement cascade.

BRIEF DESCRIPTION OF THE DRAWINGS

FIG. 3 is the UV spectra from 220-300 nm of the peak of factor J of the present invention, eluted form the hydroxylapatite column.

FIG. 4 is a graph showing the kinetics of factor J activity of the present invention as plotted on the y axis against the incubation time.

FIG. 5 is a bar graph which plots the temperature at which a hemolytic assay was performed on the x axis and the activity of factor J of the present invention (% inhibition of lysis using a hemolytic assay) on the y axis.

FIG. 6 is a reciprocal plot showing factor J of the present invention is a noncompetitive inhibitor.

DETAILED DESCRIPTION OF THE INVENTION

Figure 1:
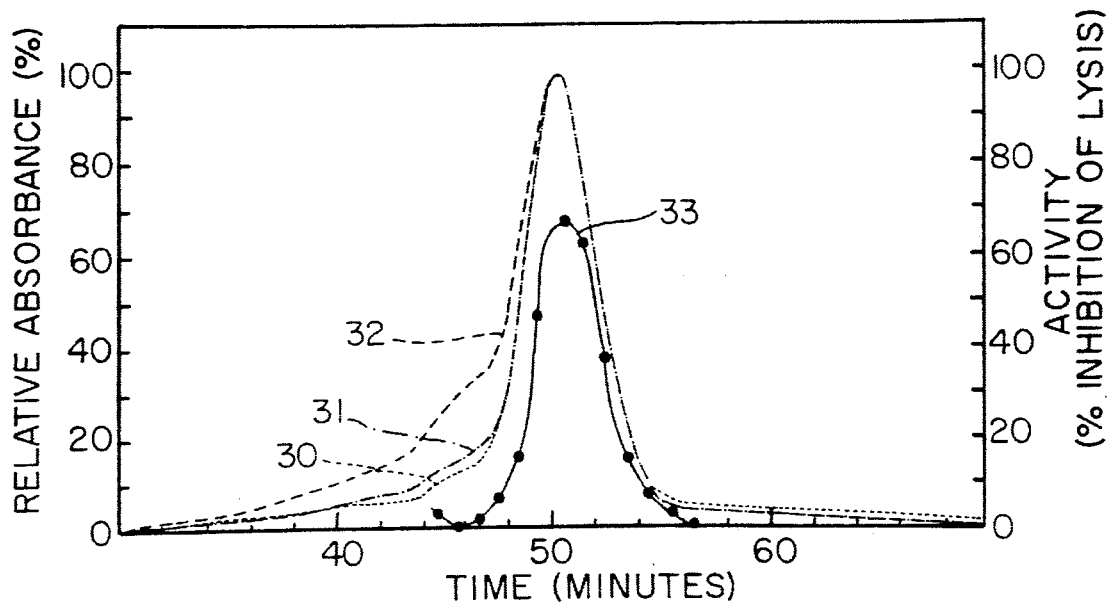
FIG. 1 is an elution profile of the purified factor J of the present invention, at three different simultaneously recorded wavelengths (A 220, 254, and 280 nm).

The present invention is based on the discovery of a new, functionally and antigenically distinct inhibitor of Cl complex association, factor J. A method is described for purifying and characterizing factor J.

The preparation starts with a sample of body fluid, such as, but not limited to, urine and serum, which has been dialyzed. The dialyzate is filtered and loaded onto an anion exchange column which has been equilibrated with dialysis buffer containing salt. The drop through fractions are collected and pooled.

The pooled fraction is diluted with the starting buffer of the QAE-Sepahadex A-50 column and loaded onto the column. Factor J is collected in the drop through and early eluted fractions of the linear salt gradient. The factor J fractions are pooled and loaded onto a heparin-Sepharose affinity column. Factor J elutes between 18 and 20 mS during a linear salt gradient when the column is equilibrated at pH 7.4 and NaCl provides the counter ion. Pools of fractions with factor J are concentrated and the buffer exchanged for the starting buffer of the Mono-Q column with inhibitors.

The concentrated solution is loaded on the Mono Q column and the drop through fractions are pooled, concentrated and the buffer exchanged with phosphate starting buffer of the hydroxylapatite column. The solution is then loaded onto a hydroxylapatite column and eluted with an increasing linear phosphate gradient. Absorbances at 220, 250 and 280 are measured and the final pools are made based on the UV absorbency and inhibitory activity.

The following example is submitted to illustrate but not limit this invention.

EXAMPLE 1

Human urine was collected from normal donors in 250ml polypropylene bottles containing stock amounts of the following inhibitors calculated to achieve the following final concentrations: 1 mM phenylmethylsufonyl fluoride (PMSF); 5 mM EDTA; 0.01% sodium azide (NaN3); 1 ug/ml leupeptin; 2 mM benzamidine-HCl, 1 ug/ml aprotinin. Upon collection of 250 ml of urine the bottle was frozen immediately at $-70°$ C. To initiate the purification procedure the requisite number of bottles to provide 800-1000 ml urine were thawed, the urine adjusted to pH 7.4 with a saturated solution of $Na_2HPO_4$, and dialyzed in 3,500 $M_r$ cut-off tubing against 4 changes of 10 liters of 10 mM sodium phosphate, pH 7.4, 2 mM EDTA, 0.01% $NaN_3$, 0.5 mM PMSF buffer until the conductivity was 2 mS, or less. The dialyzed urine was filtered through a 3 um pore polypropylene filter, available from Pall-Chisholm Company of Cranston, RI, and loaded onto a DEAE-Sephacel, available from Pharmacia LKB Biotechnology of Piscataway, N.J., column (5×50 cm) equilibrated in the dialysis buffer with 0.04 M NaCl added. The drop-through fractions were pooled and the pool diluted with 5 volumes of 5 mM Tris buffer, pH 9, and applied to a QAE-Sephadex A-50, available from Pharmacia LKB Biotechnology of Piscataway, N.J., column (5×30 cm) equilibrated in 1 mM NaCl, 5 mM Tris, pH 9. Factor J activity was about equally present in the drop-through fractions and in the early eluted fractions when a linear gradient was applied of starting buffer made with 500 mM NaCl.

Separate pools of factor J were made from the drop-through and eluted fractions, and these pools were kept separate over the subsequent purification steps, although subsequent studies indicated there was no detectable difference in the factor J from the two pools. Each pool was loaded on a heparin-Sepharose column (5×15 cm) made from crude porcine heparin coupled by cyanogen bromide to Sepharose-4B available from Pharmacia LKB Biotechnology of Piscataway, N.J., and equilibrated in 25 mM NaCl, 50 mM Tris, pH 7.4. Factor J activity eluted between 18-20 mS during a linear gradient of starting buffer made with 1.5 M NaCl. Pools of fractions with factor J activity were concentrated and buffer exchanged by ultrafiltration using a cellulose 1000 $M_r$ cut-off membrane, Spectra/Por type C, available from Spectrum Medical Industries of Los Angeles, CA, into the starting buffer for the Mono Q, 40 mM NaCl, 10 mM sodium phosphate, pH 7.8, 2 mM EDTA, 0.01% $NaN_3$, 5 mM PMSF. The concentrated pools were loaded onto a Mono Q HPLC column, HR 5/5, available from Pharmacia LKB Biotechnology of Piscataway, N.J., and the drop-through fractions pooled, concentrated, and buffer exchanged into the starting buffer for hydroxylapatite, 10 mM sodium phosphate, pH 7.4, 0.01 mM $CaCl_2$ as described above. The concentrated pools were loaded onto a HPHT hydroxylapatite HPLC column available from Bio-Rad of Richmond, CA, and eluted with a linear gradient of 10-400 mM sodium phosphate pH 7.4, 10 um $CaCl_2$. As seen in FIG. 1, absorbances at 220nm, 30, 254nm 31, and 280 nm 32 were measured simultaneously using a diode-array spectrophotometer, Hewlett-Packard #1040A, available from Hewlett-Packard Analytical Instruments of Avondale, PA. Final pools were made based on UV absorbency, 30, 31, 32, and inhibitory activity, 33.

Figure 2:
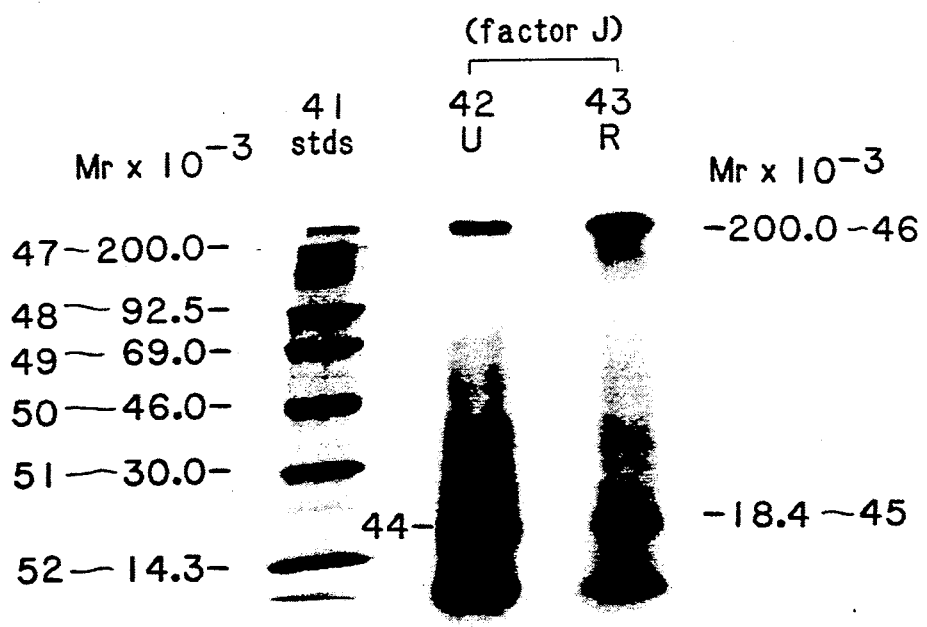
FIG. 2 is an autoradiograph of radiolabeled factor J of the present invention, after being run on a SDS-PAGE 3-20% slab gel.

The following characterization data represents specific results of factor J purified according to example 1. The factor J isolated is a protein with the following properties. FIG. 2 is an autoradiograph of unreduced, Lane 42 and reduced, Lane 43, $^{125}I$-factor J, run on a 3-20% slab SDS-PAGE gel. The major bands of factor J had a mobility of 18,400 $M_r$, 44, which did not change with reduction 45. Repeated analysis of factor J revealed a molecular weight which varied from 18,000, 44, to 22,000, 45. This variation is inherent in this method. A second prominent band was at 200,000 $M_r$, 46. Molecular weight determination was based on the $^{14}C$ labeled protein standards: myosin (200,000), phosphorylase b (92,500), bovine serum albumin (69,000) ovalbumin (46,000) carbonic anhydrase (30,000) and lysozyme (14,100). We believe the true molecular weight to be about 20,000 $M_r$ because manipulations such as storage, heating, exposure to low pH or reducing agents increased the relative amounts of the 200,000 $M_r$ and decreased the relative amount of the 20,000 $M_r$ form.

Isolated factor J has the capacity to agglutinate the erythrocytes of various species (human, rabbit, guinea pig and sheep erythrocytes have been tested, and all are positive). This agglutination becomes apparent after the factor J has passed through QAE-Sephadex. The agglutination titer and functional inhibitory titers are roughly parallel. The agglutination can be inhibited by commercial heparin.

The amino acid composition of isolated human urine factor J revealed a relatively small amount of tyrosine, about 8.7 residues per 1000, which is consistent with the poor reactivity of factor J in Folin Assays. In addition, UV spectra of purified factor J, FIG. 3, suggests a low tryptophan value which is demonstrated by the minimal absorption of purified factor J at 280nm, 55.

Results indicate that factor J is not an enzyme. Factor J inhibition occurs rapidly as can be seen in FIG. 4. Factor J reached maximum inhibitory potential within approximately five minutes, 61. Inhibitory potential was measured using a functional hemolytic assay. FIG. 5 shows that factor J activity (% inhibition) is not affected by temperature. There was no significant change in activity at temperatures ranging from 4° C., 62, to 37° C., 65. FIG. 6 shows a reciprocal plot of the data which indicates that factor J inhibition is noncompetitive, 68. This suggests that the catalytic subunit and factor J are binding reversibly, randomly and independently at different sites. Accordingly factor J could be binding to C1q directly or it could be binding to C1q once its is bound to $C1r_2s_2$.

Figure 7:
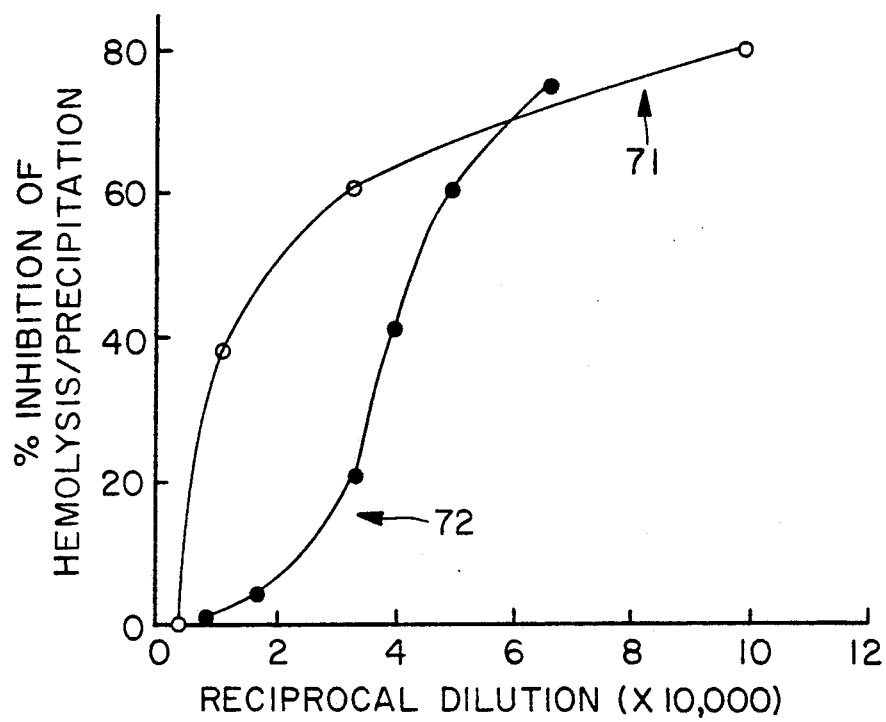
FIG. 7 is a graph plotting the dose response of factor J of the present invention when titered, x axis, in the hemolytic and C1 complex formation assays.

Factor J did inhibit association of the C1 complex as measured by factor J's ability to inhibit the precipitation of $^{125}$I-C1q in the presence of C1r and C1s, FIG. 7. This titration profile, 71, was very similar to that obtained when the dose response of factor J inhibition of C1 formation in the hemolytic assay, 72. Both assays were measured over the same concentration range of polypeptide. The difference in the shape of the inhibition curves for $^{125}$I-C1q interaction with $C1r_2s_2$, 71, and the inhibition of C1 hemolytic activity, 72, emphasizes that factor J inhibits the C1q and $C1r_2s_2$ reaction in a saturable manner consistent with direct binding to C1, whereas the inhibition of C1 hemolytic function follows a sigmoidal 72 response consistent with the complex kinetics of erythrocyte lysis induced by diluted serum.

Figure 8:
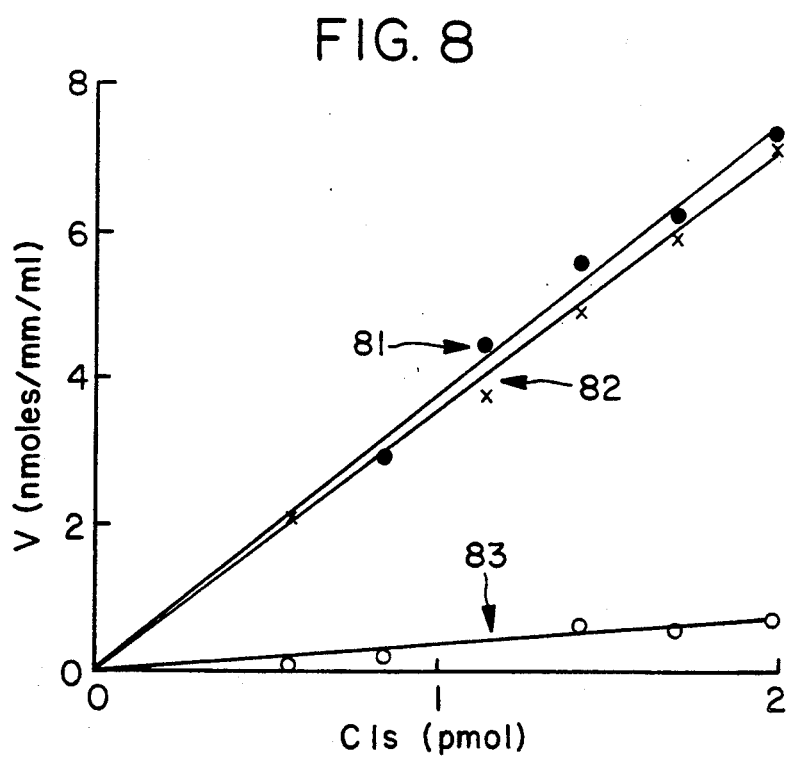
FIG. 8 is a graph showing the inability of factor J of the present invention to bind to the catalytic subunit of C1 as compared to C1 Inhibitor.
Figure 9:
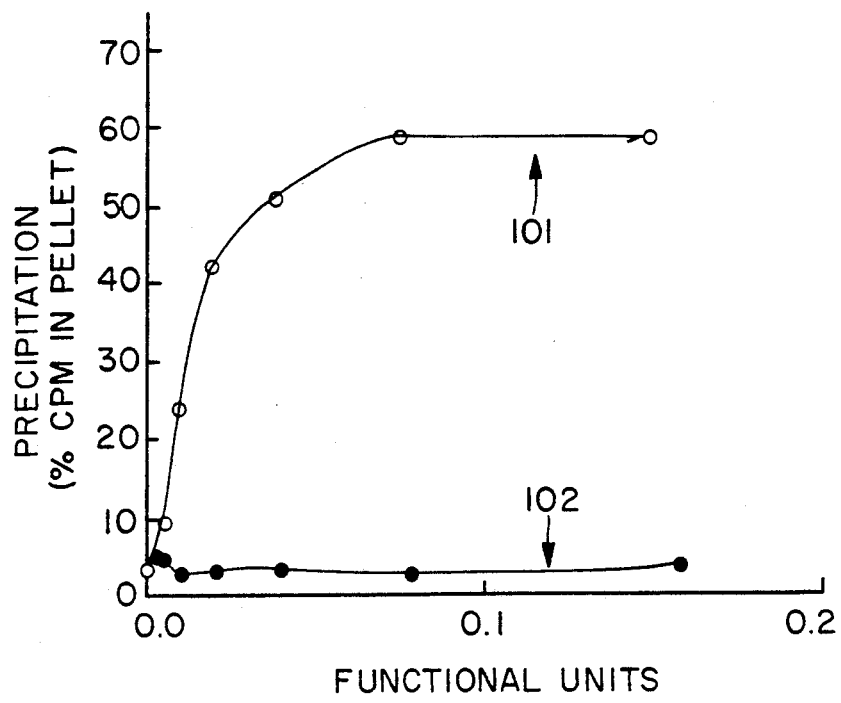
FIG. 9 is a graph of the addition of comparable amounts of functional activity of C1qINH or factor J of the present invention (x axis) plotted against the amount of bound complex $^{125}IC1$ that is precipitable.

Although factor J has been shown to inhibit C1q association with $C1r_2s_2$, the mechanisms for this inhibition are not the same as that of C1 inhibitor or C1q inhibitor. C1 inhibitor acts by binding to both catalytic subunits of C1, C1r and C1s. An assay measuring esterase activity of purified C1s, FIG. 8 compares factor J inhibition for C1s, 82, with inhibition of the C1 inhibitor for C1s, 83. As seen in FIG. 8, C1s in the presence of factor J, 82, or buffer alone, 81, show comparable amounts of esterase activity, whereas, the addition of C1 Inhibitor resulted in a significant decrease in C1 esterase activity, 83. C1q inhibitor acts by binding to C1q and thereby preventing the catalytic subunits from binding to C1q. FIG. 9 demonstrates that factor J does not bind to C1q under conditions in which the C1q Inhibitor could bind C1q. Partially purified C1q inhibitor bound to and precipitated $^{125}$I-C1q, 101, whereas, purified factor J did not bind to $^{125}$I-C1q in the fluid phase to permit precipitation of the $^{125}$I-C1q, 102.

Factor J can also inhibit the human alternative complement pathway in an assay utlizing sheep erythrocytes bearing human C3b, and purified factor D, factor B, and peperidin. The process step in the alternative pathway where factor J inhibits is not yet known.

Figure 10:
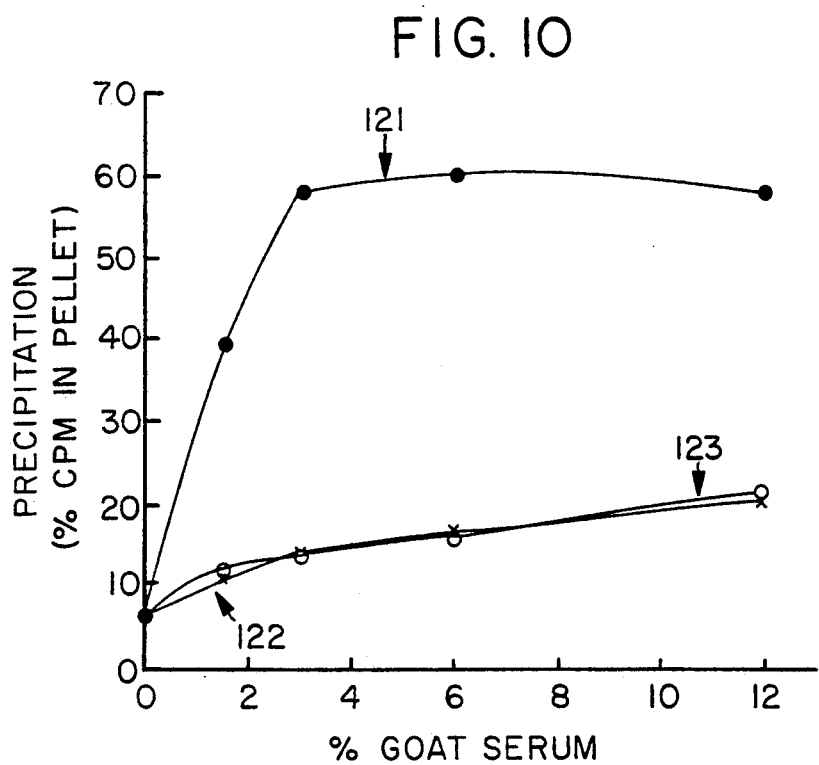
FIG. 10 is a graph indicating the presence of the factor J antigen of the present invention in human serum.
Figure 11:
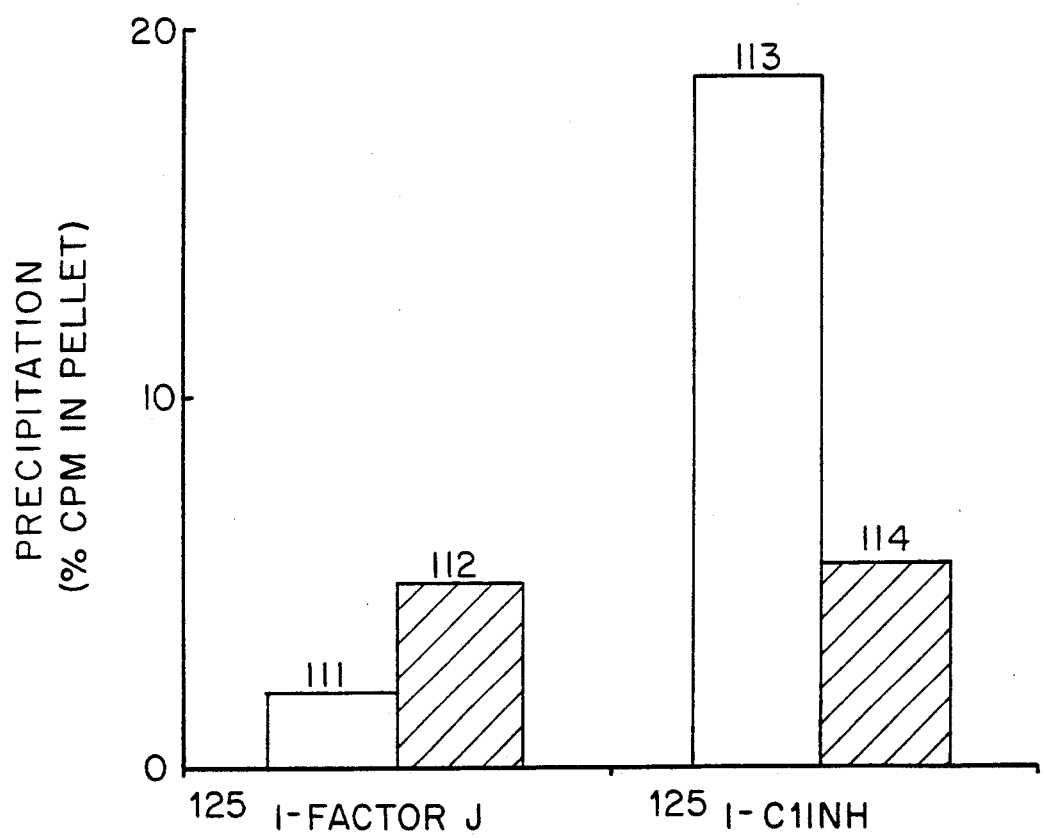
FIG. 11 is a bar graph showing the antigenic difference between Cl Inhibitor and factor J of the present invention.

Antigenic results indicate that factor J is present in human serum and it does not cross react with antigen for C1 Inhibitor. FIG. 10 shows that goat anti-human serum precipitates radiolabeled factor J, 121, above the background level precipitated by normal goat serum, 122. Goat anti-C1q, 123, did not cause any precipitation of radiolabeled factor J above background. In addition, FIG. 11 demonstrates that factor J is not antigenically related to C1 Inhibitor. The anti-C1 Inhibitor did not specifically absorb the factor J, 111, as compared with anti-5, a control, 112, whereas the anti-C1 Inhibitor was able to specifically absorb $^{125}$I-C1 Inhibitor under the same conditions, 113.

Having above indicated a preferred embodiment of the present invention it will occur to those skilled in the art that modifications and alternatives can be practiced within the spirit and scope of the invention. It is accordingly intended to define the scope of the invention only as indicated in the following claims.

EXAMPLE 2

Approximately 100-200 ml of serum is collected and saturated to 15% (weight/weight) with polyethylene glycol available from Sigma Chemical Co of St. Louis, MO. The saturated solution is kept at 4° C. for 30 minutes and then centrifuged. The precipitate is collected and the supernatant is discarded.

The precipitate is solubilized with pH 7.5 NaCl phosphate buffer and further diluted with water to adjust the solution to a conductivity of about 4 mS. This adjusted solution is loaded onto a DEAE-Sephacel, available from Pharmacia LKB Biotechnology of Piscataway, N.J., column (5×50 cm). The non-absorbed material is collected, pooled and adjusted to pH 9. The adjusted material is then applied to a QAE-Sephadex A-50, available from Pharmacia LKB Biotechnology of Piscataway, N.J., column (5×30 cm) equilibrated in 1 mM NaCl, 5 mM Tris, pH 9. The effluent is collected, pooled and adjusted to pH 7.2.

The adjusted effluent pool was loaded on a heparin-Sepharose column (5×15 cm) made from crude porcine heparin coupled by cyanogen bromide to Sepharose-4B, available from Pharmacia LKB Biotechnology of Piscataway, N.J., and equilibrated in 25 mM NaCl, 50mM Tris, pH 7.4. Factor J activity eluted between 18-20 mS during a linear gradient of starting buffer made with 1.5 M NaCl. Pools of fractions with factor J activity were concentrated and buffer exchanged by ultrafiltration using a cellulose 100 $M_r$ cut-off membrane, Spectra/Por type C, available from Spectrum Medical Industries of Los Angeles, CA, into the starting buffer for the Mono Q column, 40 mM NaCl, 10 mM sodium phosphate, pH 7.8, 2 mM EDTA, 0.01% $NaN_3$, 5 mM PMSF. The concentrated pools were loaded onto a Mono Q HPLC column, HR 5/5, available from Pharmacia LKB Biotechnolgy of Piscataway, N.J., and the drop-through fractions pooled, concentrated, and buffer exchanged into the starting buffer for the hydroxylapatite column, 10 mM sodium phosphate, pH 7.4, 0.01 mM $CaCl_2$. The concentrated pools were loaded onto a HPHT hydroxylapatite HPLC column available from Bio-Rad of Richmond, CA, and eluted with a linear gradient of 10-400 mM sodium phosphate pH 7.4, 10 uM $CaCl_2$. Pools were made based on UV absorbency and inhibitory activity. This pool is then applied to a Vydac C4 reverse phase column, available from Vydac of Hisperia, CA, which has been equilibrated with 0.1% trifluoracetic acid (TFA) in water. The factor J is eluted in a gradient made with the equilibration buffer and 95% acetonitrile in 5% water, 0.1% TFA. The elution rate is 1ml/min and the factor J peak elutes at about 19 min in a 30 minute run. The fractions are dried down and reconstituted in 0.1 M $NH_4HCO_3$ buffer for assaying.

In practice, factor J is isolated, purified and administered in a therapeutic amount to inhibit the undesirable activation of the complement cascade system.

What is claimed is:

1. A purified and isolated factor J with the following characteristics:
   a) elutes as a single peak from a hydroxylapatite column with symmetrical U.V. absorbance at 220, 250 and 280 nm;
   b) a tyrosine composition of about 8.7 residues per 1000 residues;
   c) inhibits Cl;
   d) does not inhibit Cls;
   e) dissociates intact Cl;
   f) prevents Cl assembly form subcomponents;
   g) when subjected to sodium dodecyl sulfate-polyacrylamide gel electrophoresis, migrates to a region corresponding to a molecular weight between 18,000 and 22,000 Daltons, whether reduced or non-reduced;
   h) agglutinates the erythrocytes from several species of mammals including human, rabbit, guinea pig and sheep and this agglutination is inhibited by heparin;
   i) inhibits the alternative complement pathway; and
   j) is free of other known inhibitors of Cl.

2. The purified inhibitor of claim 1 wherein said inhibitor, factor J, is derived from a body fluid.

3. The purified inhibitor, factor J, of claim 2 wherein said body fluid is urine.

* * * * *